(12) United States Patent
Delnevo

(10) Patent No.: US 6,952,963 B2
(45) Date of Patent: Oct. 11, 2005

(54) METHOD FOR DETECTING A LIQUID LEVEL IN A CONTAINER IN A CIRCUIT AND A DIALYSIS MACHINE FOR ACTUATING THE METHOD

(75) Inventor: Annalisa Delnevo, Santa'Agata Bolognese (IT)

(73) Assignee: Gambro Dasco S.p.A., Medolla (IT)

( * ) Notice: Subject to any disclaimer, the term of this patent is extended or adjusted under 35 U.S.C. 154(b) by 170 days.

(21) Appl. No.: 10/443,996

(22) Filed: May 23, 2003

(65) Prior Publication Data

US 2004/0231414 A1 Nov. 25, 2004

(51) Int. Cl.$^7$ .............................................. G01F 17/00
(52) U.S. Cl. ...................... 73/290 B; 73/149; 73/290 R
(58) Field of Search ....................... 73/149, 301, 290 B

(56) References Cited

U.S. PATENT DOCUMENTS

| 4,085,046 A | * | 4/1978 | Saporito, Jr. .................. 210/90 |
| 4,121,094 A | * | 10/1978 | DiVito et al. .................. 377/24 |
| 4,535,627 A | * | 8/1985 | Prost et al. ............... 73/290 B |
| 5,421,208 A | * | 6/1995 | Packard et al. ............... 73/861 |
| 5,578,223 A | * | 11/1996 | Bene et al. .................... 210/85 |
| 5,670,710 A | * | 9/1997 | Atkinson .................... 73/61.45 |

* cited by examiner

Primary Examiner—Hezron Williams
Assistant Examiner—Katina Wilson
(74) Attorney, Agent, or Firm—Finnegan, Henderson, Farabow, Garrett & Dunner, L.L.P.

(57) ABSTRACT

A container of a dialysis machine has a determined shape and a known volume occupied in part by a volume of a mass of blood; a remaining part is occupied by a volume of a mass of gas. A disturbance is induced in a combined mass of the liquid and the gas in the container and an entity of the disturbance is measured. Measurements of pressure in the container before and after the disturbance are taken, the volume of gas is calculated using a function correlated to a gas law, and the volume and level of the liquid in the container are derived after the volume occupied by the gas is calculated.

12 Claims, 1 Drawing Sheet

METHOD FOR DETECTING A LIQUID LEVEL IN A CONTAINER IN A CIRCUIT AND A DIALYSIS MACHINE FOR ACTUATING THE METHOD

BACKGROUND OF THE INVENTION

The invention relates to a method for detecting a liquid level in a container of a circuit.

In particular, the invention relates to a method for detecting a level of blood in a container of a circuit of a dialysis machine, to which the present application will make specific reference without in any way limiting the scope of the invention.

A known-type dialysis machine comprises a first blood circulation circuit and a second circulation circuit for the dialysate liquid. The first circuit and the second circuit are connected to a filter for conveying, respectively, the blood and dialysate liquid through the filter, which is provided with a semi-permeable membrane separating the blood from the dialysate liquid. The first circuit is provided with a container, known as a drip chamber, into which the blood is supplied from a first tract of the first circuit, and drips and collects on the bottom of the container, thence to enter a second tract of the first circuit. The container has the function of preventing air from becoming trapped in the blood in the form of bubbles, which might cause embolisms once the treated blood was returned to the cardio-vascular system of the patient. To guarantee the safest possible treatment the blood level in the container must be maintained within an optimum range of values, below which the possibility of creating air bubbles in the blood returning to the patient exists, and above which the pressure increases to unacceptable values which are dangerous for the patient.

To solve this problem, the prior art teaches blood level detection devices, comprising an optical emitter arranged on one side of the container and an optical reader arranged on another side of the container at an optimal level. This sensor device detects only if the level of blood is above or below the optimal level and is therefore unable to provide an accurate level reading. To obtain a more accurate blood level reading, the above-described sensor device has been modified to include two optical emitters and two optical readers suitably arranged, which provide an acceptability interval parameter of the blood level.

Still more accurate readings can be achieved with a plurality of optical emitters and a plurality of optical readers, which define a plurality of intervals and detect the interval which the blood level is at.

The above-described sensor devices are based on the principle of emission and reception of a signal and become progressively more complicated as the need for more accurate blood level readings increases, since the number of emitters and readers increases together with the need for accuracy.

SUMMARY OF THE INVENTION

The main aim of the present invention is to provide a level sensor method in a container of a circuit, which method is without the drawbacks inherent in the prior art and which, in particular, provides a high degree of accuracy and requires the use of simple and economical equipment.

The present invention provides a method for detecting a level of liquid in a container connected to a circuit, the container being of a determined shape and having a known volume occupied in part by a volume of a mass of liquid and, in a remaining part, by a volume of a mass of gas, the method being characterised in that it determines the volume of the mass of gas in order to calculate the volume of the liquid and the level thereof.

The present invention also relates to a dialysis machine.

The present invention provides a dialysis machine for actuating the method characterized in that it comprises a pressure sensor for detecting the pressure of the mass of gas in the container.

BRIEF DESCRIPTION OF THE DRAWINGS

The present invention will now be described with reference to the accompanying figures of the drawings, which illustrate a non-limiting embodiment thereof, and in which.

DETAILED DESCRIPTION

Figure 1:
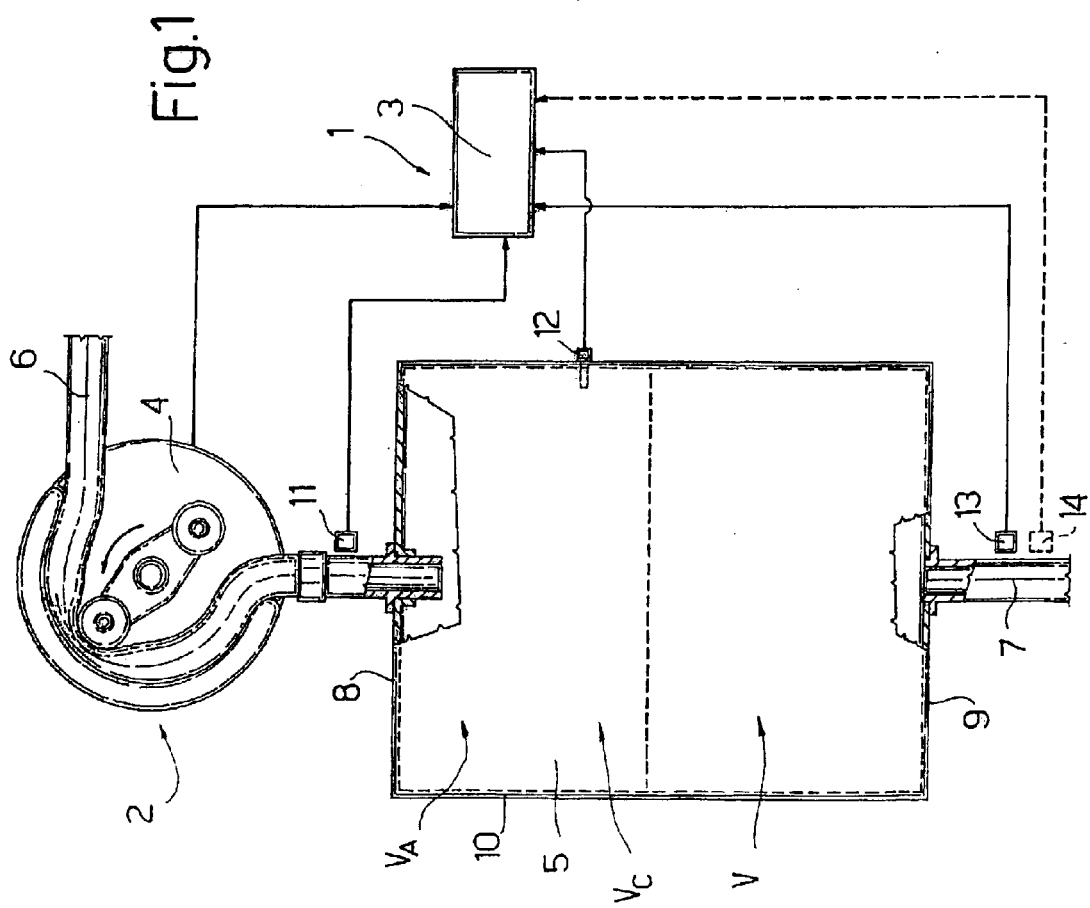
FIG. 1 is a schematic side elevation, with some parts removed for reasons of clarity and other parts shown in section, of a dialysis machine and a circuit associated to the dialysis machine.

With reference to FIG. 1, 1 denotes in its entirety a dialysis machine comprising a blood circulation circuit 2, which during operation is connected up to the cardio-vascular system of a patient, in order to convey the patient's blood during a dialysis treatment. At the end of the treatment the circuit 2 is eliminated as it is disposable as special waste after one use only.

The dialysis machine 1 comprises a control unit 3 and a peristaltic pump 4 for circulating the blood in the circuit 2.

The circuit 2 comprises a container 5, a supply branch 6 for taking blood to the container 5 which is trained about a peristaltic pump 4, and a return branch 7 taking the blood from the container 5. The container 5 comprises an upper wall 8, through which the supply branch 6 is connected to the container 5, a lower wall, to which the return branch 7 is attached, and a lateral wall 10.

The machine 1 comprises a pressure sensor 11 arranged along the supply branch 6 directly upstream of the container 5, a temperature sensor 12 arranged along the lateral wall 10 of the container 5, and a pressure sensor 13 arranged along the return branch 7. Alternatively, the pressure sensor 13 can be substituted by a flow rate sensor 14, which is illustrated in a broken line in FIG. 1, and detects the flow rate $Q_{out}$ of blood exiting from the container 5. The pressure sensor 13 reads the pressure $P_b$ at a predetermined point in the branch 7 and enables calculation of flow rate $Q_{out}$ by means of a constant H of known loss of head along the return branch 7 comprised between the container 5 and the pressure sensor 13. The pressure sensor 11, the temperature sensor 12, and the pressure sensor 13 are connected to the control unit 3, which is connected in turn to the peristaltic pump 4 for controlling and commanding the peristaltic pump 4 and for reading, at the same time, the flow rate of the blood $Q_{in}$ introduced into the container 5 by the peristaltic pump 4.

During operation, the blood removed from the patient is fed into the container 5 through the supply branch 6, where it drips and is collected on the bottom of the container 5 from which it is removed through the return branch 7.

The container 5 is hermetically sealed and is connected only to the supply branch 6 and the return branch 7. The container 5 exhibits a constant volume $V_C$, which is in part occupied by a mass M of blood corresponding to a volume V of blood and a mass N of air which corresponds to a volume $V_A$ at a predetermined pressure P.

The pressure sensor 11 monitors the air pressure P (which corresponds to the blood pressure in the container 5) present in the upper part of the container 5 and transmits the values detected to the control unit 3, while the temperature sensor 14 monitors the temperature T of the air contained in the container 5 and transmits the read values to the control unit 3, which receives the measurements of the flow rate at inflow $Q_{in}$ and the flow rate at outflow $Q_{out}$.

Determination of the level of blood in the container 5 is done by means of a calculation of the volume V of blood, which is determined as the difference between the volume $V_C$ of the container 5 and the volume $V_A$ of the air, which volume $V_A$ is determined by means of a function correlated to a law relating to gases on the basis of the values transmitted to the control unit 3. As the calculation of the volume of air done using a gas law, such as Perfect Gas Law, (also known as Boyle-Mariotte's Law) namely PV=JRT, also requires measurement of the number J of moles of air present in the container 5, as well as two easily measurable amounts i.e. pressure P and temperature T, the method is based on the principle of disturbance of the overall mass contained in the container 5.

This in effect means inducing a change in the mass M of blood in the container 5, calculating the entity of the ensuing disturbance corresponding to the variation in the volume V of blood, which can be calculated from the integral of the balance of the blood inflowing flow rate $Q_{in}$ and the outflowing flow rate $Q_{out}$, and detecting the effects of the disturbance, which correspond to a change in the pressure P of the air, the temperature T remaining practically constant. With the disturbance caused to the mass M, the volume $V_A$ occupied by the air can be calculated and so can the volume V and level of the blood.

The present invention presupposes that the blood is a non-compressible liquid and that the measurement of the level will be more accurate according to how true the non-compressible aspect is. Tests have shown that blood at the machine working pressures in dialysis machines does in fact behave as a non-compressible liquid: there therefore exists a directly proportional relationship between the mass M of blood and the volume V of blood in the container 5.

In order to explain the invention in more detail, there follows an example relating to the calculation of the level following creation of a disturbance in the mass M of blood.

EXAMPLE 1

The container 5 contains, at a determined moment $t_0$, a volume V of blood and the blood inflows at a flow rate $Q_{in}$ by means of the peristaltic pump 4, while outflowing blood from the container 5 occurs at a flow rate $Q_{out}$. The overall volume of the container 5 is $V_C$, thus the volume $V_A$ occupied by the air at $t_0$ is $V_C-V$, while the air pressure at $t_0$ is equal to $P_0$. The peristaltic pump 4 operation modes cause a variation in the inflow flow rate $Q_{in}$ and the outflow flow rate $Q_{out}$ and therefore cause a cyclic variation in the volume V of blood in the container 5. Thus, at a determined moment $t_1$ the change in the blood volume is $V_D$ and the following expression of the relations results:

$P_0(V_C-V) = J R T$ at moment $t_0$ $P_1(V_C-V-V_D) = J R T$ at moment $t_1$ in which the number J of moles of air remains constant, R is a constant, and the temperature T is considered to be constant. From the above expressions the following can be derived:

$P_0(V_C-V) = P_1(V_C-V-V_D)$ in which $$V_D = \int_{t_0}^{t_1}(Q_{in}-Q_{out})dt$$

from which the volume V at moment $t_0$ is derived as $$V = V_C - \frac{P_1 \cdot V_D}{P_1 - P_0}$$

and the volume at $t_1$ is $V+V_D$.

The value of V can be derived from the inflow flow rate $Q_{in}$ and the outflow flow rate $Q_{out}$, i.e. the disturbance caused, and from the pressure P change, i.e. the effect of the disturbance. From the value of V the level of blood contained in the container can be determined. In this case, the circuit 2 must be equipped with the flow rate sensor 14 in order to detect the outflowing flow rate $Q_{out}$ from the container 5; and the control of the peristaltic pump 4 r.p.m. must provide the inflowing flow rate $Q_{in}$.

Alternatively, on reading the outflowing flow rate $Q_{out}$, the pressure $P_b$ read at a determined point along the return branch 7 enables the outflow flow rate to be determined using the following equation:

$Q_{out} = H \cdot (P-P_b)$, in which H is the loss of head in the return branch 7 comprised between the container 5 and the pressure sensor 13.

The temperature T is monitored only for the purpose of determining if there occur any relevant changes in the temperature T and, therefore, for the purpose of evaluating whether the measurement taken is valid. However, it has generally been the case that the change in temperature T is not appreciable and the temperature sensor 12 can be left out. The function PV=JRT can be rewritten as PV=NK in which K is a constant that comprises the value of the temperature T and the constant R of the gas, while the number J of moles of air is related to the mass N of air.

Figure 2:
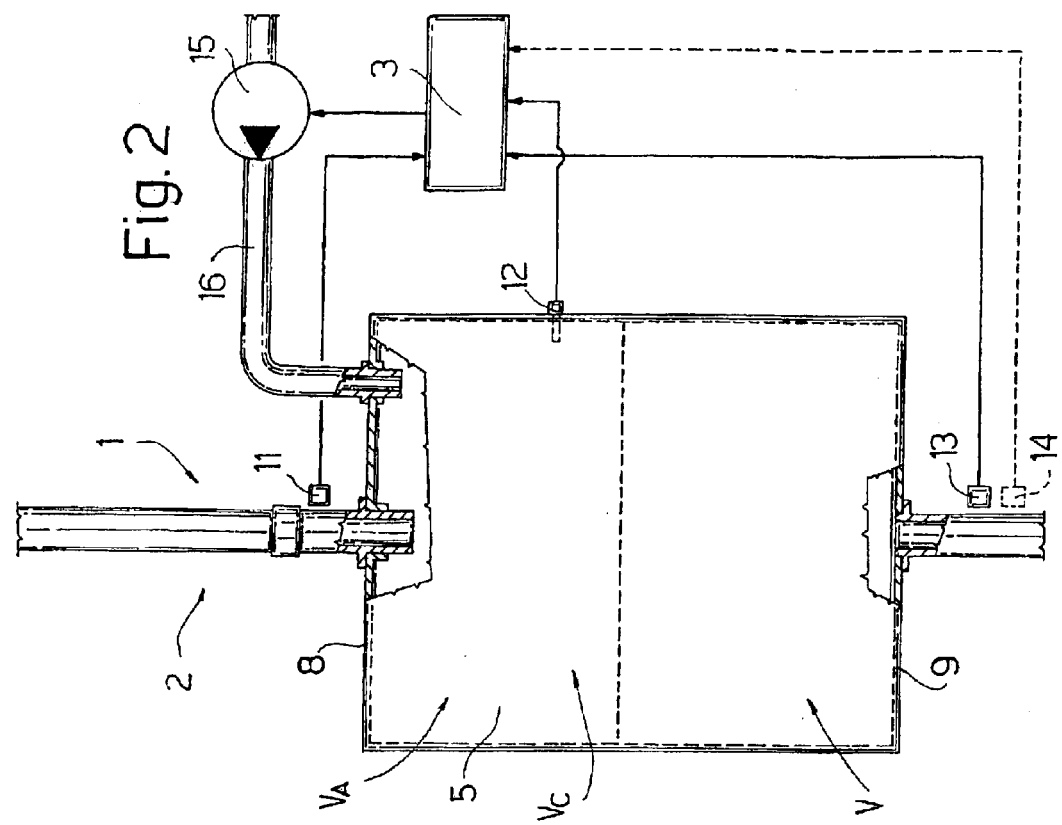
FIG. 2 is a schematic side elevation, with some parts removed for reasons of clarity and other parts shown in section, of a variant of the machine of FIG. 1.

In the variant of FIG. 2, the peristaltic pump 4 is left out and the machine 1 comprises a pump 15 connected to the upper wall 8 of the container 5 by a conduit 16 and controlled by the control unit 3. The pump 15 is a positive displacement pump supplying an air flow rate $Q_A$ which varies according to the number of pump 15 revolutions per minute.

In this case, the function PV=NK is used to evidence the variation in the mass of gas determined by the pump 15. During operation, the pump 15 sends a determined mass DN of air into the container 5 to calculate the volume $V_A$ of air on the basis of the disturbance in the pressure P. To clarify this calculation process, a further example is now given.

EXAMPLE 2

The container 5 contains a determined volume V of blood which corresponds to a mass M of blood and both the blood supply and evacuation are interrupted. The volume occupied by the air is $V_A$, which corresponds to a mass N of air. The overall volume of the container 5 is $V_C$, therefore the volume occupied by the air is $V_C-V$, while the pressure detected at a determined moment t0 is $P_0$. The slight pressure variations P lead to establish that the temperature T can be considered constant.

In the above established state, at moment t0 the following is a valid expression:

$$P_0(V_C - V) = N_0 K \quad \text{a)}$$

The pump 15 induces a disturbance in the container 5, which is a variation in the mass $N_0$ of air, by injecting a mass DN of air into the container 5, to bring the mass of air up to a level expressed by:

$$N_1 = N_0 + DN. \quad \text{b)}$$

The disturbance in the mass of air determines a variation in pressure P inside the container 5. Following the variation in mass, at moment $t_1$ the following is a valid expression:

$$P_1(V_C - V) = N_1 K. \quad \text{c)}$$

Putting the three expressions together (a, b, c), unknowns $N_0$, $N_1$ and V are derived, while $P_0$ and $P_1$ are measured, $V_C$ is known from the geometry of the container 5 and DN is derived from the following equation:

$$DN = \int_{t_0}^{t_1} Q_A dt$$

in which $Q_A$ is the flow rate of the pump 4.

Once V has been determined, as the geometry of the container 5 is known, the level of blood in the container can be deduced. In this case the control unit 3 receives the values of the pressure $P_0$ before the disturbance, the values of flow rate $Q_A$ of the peristaltic pump 4 for determining the entity of the disturbance, and the values $P_1$ after the disturbance. The start of the disturbance enables a relatively easy measurement to be made, namely the flow rate of air $Q_A$ to obviate the measurement of the mass $N_0$ contained in the container 5. The flow rate of air $Q_A$ in terms of mass can be derived from the measurement of the flow rate $Q_A$ in terms of volume, the compression ratio of the pump 4 and the fact that the air is taken in at room temperature.

In examples 1 and 2, reference has been made to Perfect Gas Law, though the method of the present invention is valid for determining the level even when other gas laws are used that relate the volume $V_A$, the pressure P, the mass N and the temperature T and other properties that can be considered constant.

Tests carried out by the applicant have demonstrated that the reading of the pressure P before and after the disturbance is vital in calculating the volume of air $V_A$ and, therefore, the level, while monitoring the temperature T is not necessary for the calculation of the level, as it is supposed that variations in mass M and N induce isothermal transformation. The reading of the temperature can be considered constant and, therefore, provides an evaluation parameter regarding the reliability of the measurement.

What is claimed:

1. A method for determining a liquid level in a container of known volume occupied in part by a liquid and in part by a gas, the method comprising the steps of:
   taking the liquid to the container;
   evacuating the liquid from the container;
   creating a liquid level in the container while the liquid is taken to and evacuated from the container;
   varying at least one of a mass of the gas and a mass of the liquid in the container;
   detecting pressure values in the container before and after said variation of at least one of a mass of the gas and a mass of the liquid in the container; and
   determining the liquid level in the container from said detected pressure values.

2. The method of claim 1, wherein the step of determining the liquid level comprises the step of calculating the volume of the gas in the container on the basis of a gas law which interrelates mass, volume, temperature and pressure of the gas.

3. The method of claim 1, comprising the step of detecting said variation of at least one of a mass of the gas and a mass of the liquid in the container.

4. The method of claim 1 wherein said variation of at least one of a mass of the gas and a mass of the liquid in the container is of an entity which determines an isothermal transformation.

5. The method of claim 1, wherein said liquid mass variation is directly proportional to a variation of the volume of the liquid in the container, said liquid being non-compressible.

6. The method of claim 5, wherein said liquid volume variation is equal to an integral of the difference between a liquid flow rate in inflow to the container and a liquid flow rate in outflow from the container between an initial moment and a final moment.

7. The method of claim 6, comprising the step of measuring the liquid flow rate in inflow to the container and the liquid flow rate in outflow from the container.

8. The method of claim 6, comprising the steps of:
   measuring the liquid flow rate in inflow to the container and a liquid pressure at a point of a circuit downstream of the container; and
   calculating the liquid flow rate in outflow as a function of a known loss of head in a tract of the circuit situated between the container and said point of the circuit.

9. The method of claim 1, wherein the step of varying the mass of the gas in the container comprises the step of supplying a gas to the container by means of a gas supply conduit connected to the container and a gas supply pump arranged along said gas supply conduit.

10. The method of claim 1 comprising the step of measuring the temperature of the gas in the container.

11. The method of claim 1, wherein said liquid comprises blood and said gas comprises air.

12. The method of claim 1, wherein said liquid is circulated through the container by means of a peristaltic pump.

* * * * *